US010596394B2

(12) United States Patent
Simon et al.

(10) Patent No.: US 10,596,394 B2
(45) Date of Patent: Mar. 24, 2020

(54) BEAM ANGLE DIRECTION DETERMINATION

(71) Applicant: SUN NUCLEAR CORPORATION, Melbourne, FL (US)

(72) Inventors: William E. Simon, Melbourne, FL (US); Jakub Kozelka, Melbourne, FL (US); Kai Wundke, Melbourne, FL (US); Jie Shi, Melbourne, FL (US)

(73) Assignee: Sun Nuclear Corporation, Melbourne, FL (US)

( * ) Notice: Subject to any disclaimer, the term of this patent is extended or adjusted under 35 U.S.C. 154(b) by 341 days.

(21) Appl. No.: 15/663,442

(22) Filed: Jul. 28, 2017

(65) Prior Publication Data

US 2018/0028840 A1 Feb. 1, 2018

Related U.S. Application Data

(60) Provisional application No. 62/367,932, filed on Jul. 28, 2016.

(51) Int. Cl.
*A61N 5/10* (2006.01)

(52) U.S. Cl.
CPC ......... *A61N 5/1082* (2013.01); *A61N 5/1048* (2013.01); *A61N 5/1049* (2013.01);
(Continued)

(58) Field of Classification Search
CPC ... A61N 5/1082; A61N 5/1049; A61N 5/1069
See application file for complete search history.

(56) References Cited

U.S. PATENT DOCUMENTS

| 759,608 A | 5/1904 | Harper |
| 1,239,145 A | 9/1917 | Wantz |

(Continued)

FOREIGN PATENT DOCUMENTS

| CA | 2718408 | 9/2009 |
| DE | 102009039345 A1 | 3/2011 |

(Continued)

OTHER PUBLICATIONS

McDermott et al.; "Replacing Pretreatment Verification with In Vivo EPID Dosimetry for Prostate IMRT"; International Journal of Radiation: Oncology Biology Physics, Pergamon Press, USA, vol. 67, No. 5, Mar. 28, 2007, pp. 1568-1577, XP022101268, ISSN: 0360-3016, DOI: 10.1016/J.IJROBP.2006.11.047.

(Continued)

*Primary Examiner* — Hugh Maupin
(74) *Attorney, Agent, or Firm* — Pillsbury Winthrop Shaw Pittman LLP

(57) ABSTRACT

A system is disclosed that includes a radiation therapy device with a gantry. The radiation therapy device is configured to deliver a radiation beam at an angle determined by orientation of the gantry. Also, a pair of radiation detectors are located at a fixed position to receive radiation originating from the radiation beam. Each of the radiation detectors in the pair generate differing responses to the radiation beam at the angle. The system further includes computer hardware configured to perform operations that determine the angle of the gantry utilizing the differing responses from the pair of radiation detectors.

19 Claims, 10 Drawing Sheets

(52) U.S. Cl.
CPC ......... *A61N 5/1069* (2013.01); *A61N 5/1075* (2013.01); *A61N 5/1081* (2013.01); *A61N 2005/1061* (2013.01); *A61N 2005/1087* (2013.01)

(56) References Cited

U.S. PATENT DOCUMENTS

| | | |
|---|---|---|
| 2,818,510 A | 12/1957 | Hansheinrich |
| 3,033,985 A | 5/1962 | Ben |
| 3,394,258 A | 7/1968 | Schleiger |
| 3,433,953 A | 3/1969 | Sweet |
| 3,665,762 A | 5/1972 | Domen |
| 3,783,251 A | 1/1974 | Pavkovich |
| 3,790,794 A | 2/1974 | Murray |
| 3,980,885 A | 9/1976 | Steward |
| 4,058,832 A | 11/1977 | Vagi |
| 4,063,097 A | 12/1977 | Barrett |
| 4,107,531 A | 8/1978 | Garratt |
| 4,157,472 A | 6/1979 | Barrett |
| 4,312,224 A | 1/1982 | Domen |
| 4,450,440 A | 5/1984 | White |
| 4,455,609 A | 6/1984 | Inamura |
| 4,613,754 A | 9/1986 | Vinegar |
| 4,729,099 A | 3/1988 | Iverson |
| 4,765,749 A | 8/1988 | Bourgade |
| 4,777,442 A | 10/1988 | Rosenthal |
| 4,887,287 A | 12/1989 | Cobben |
| 5,099,505 A | 3/1992 | Seppi |
| 5,160,337 A | 11/1992 | Cosman |
| 5,262,649 A | 11/1993 | Antonuk |
| 5,388,142 A | 2/1995 | Morris |
| 5,394,452 A | 2/1995 | Swerdloff |
| 5,596,653 A | 1/1997 | Kurokawa |
| 5,602,892 A | 2/1997 | Llacer |
| 5,621,214 A | 4/1997 | Sofield |
| 5,622,187 A * | 4/1997 | Carol .............. A61N 5/1049 128/897 |
| 5,627,367 A | 5/1997 | Sofield |
| 5,635,709 A | 6/1997 | Sliski |
| 5,640,436 A | 6/1997 | Kawai |
| 5,661,310 A | 8/1997 | Jones |
| 5,704,890 A | 1/1998 | Bliss |
| 5,712,482 A | 1/1998 | Gaiser |
| 5,873,826 A | 2/1999 | Gono |
| 5,965,214 A | 10/1999 | Crossfield |
| 6,038,283 A | 3/2000 | Carol |
| 6,054,924 A | 4/2000 | Dames |
| 6,076,007 A | 6/2000 | England |
| 6,125,335 A | 9/2000 | Simon |
| 6,131,690 A | 10/2000 | Galando |
| 6,144,300 A | 11/2000 | Dames |
| 6,148,272 A | 11/2000 | Bergstrom |
| 6,175,761 B1 | 1/2001 | Frandsen |
| 6,204,766 B1 | 3/2001 | Crossfield |
| 6,230,972 B1 | 5/2001 | Dames |
| 6,257,552 B1 | 7/2001 | Crow |
| 6,261,219 B1 | 7/2001 | Meloul |
| 6,301,329 B1 | 10/2001 | Surridge |
| 6,323,769 B1 | 11/2001 | Dames |
| 6,345,114 B1 | 2/2002 | Mackie |
| 6,364,529 B1 | 4/2002 | Dawson |
| 6,369,965 B1 | 4/2002 | Dames |
| 6,398,710 B1 | 6/2002 | Ishikawa |
| 6,486,655 B1 | 11/2002 | Crossfield |
| 6,516,046 B1 | 2/2003 | Froehlich |
| 6,535,574 B1 * | 3/2003 | Collins ............... A61N 5/1049 378/20 |
| 6,535,756 B1 | 3/2003 | Simon |
| 6,552,347 B1 | 4/2003 | Dimcovski |
| 6,560,311 B1 | 5/2003 | Shepard |
| 6,577,237 B1 | 6/2003 | Dames |
| 6,594,336 B2 | 7/2003 | Nishizawa |
| 6,595,419 B1 | 7/2003 | Doyle |
| 6,609,626 B2 | 8/2003 | Young |
| 6,609,826 B1 | 8/2003 | Fujii |
| 6,626,569 B2 | 9/2003 | Reinstein |
| 6,636,622 B2 | 10/2003 | Mackie |
| 6,648,503 B2 | 11/2003 | Tanaka |
| 6,712,508 B2 | 3/2004 | Nilsson |
| 6,788,759 B2 | 9/2004 | Op De Beek |
| 6,799,068 B1 | 9/2004 | Hartmann |
| 6,810,107 B2 | 10/2004 | Steinberg |
| 6,810,108 B2 | 10/2004 | Clark |
| 6,833,707 B1 | 12/2004 | Dahn |
| 6,839,404 B2 | 1/2005 | Clark |
| 6,853,702 B2 | 2/2005 | Renner |
| 6,888,919 B2 | 5/2005 | Graf |
| 6,904,119 B2 | 6/2005 | Oikawa |
| 6,904,125 B2 | 6/2005 | Van Dyk |
| 6,904,162 B2 | 6/2005 | Robar |
| 6,974,254 B2 | 12/2005 | Paliwal |
| 6,990,368 B2 | 1/2006 | Simon |
| 6,992,309 B1 | 1/2006 | Petry |
| 7,016,454 B2 | 3/2006 | Warnberg |
| 7,065,812 B2 | 6/2006 | Newkirk |
| 7,076,023 B2 | 7/2006 | Ghelmansarai |
| 7,098,463 B2 | 8/2006 | Adamovics |
| 7,116,749 B2 | 10/2006 | Besson |
| 7,127,028 B2 | 10/2006 | Sendai |
| 7,127,030 B2 | 10/2006 | Tamegai |
| 7,142,634 B2 | 11/2006 | Engler |
| 7,193,220 B1 | 3/2007 | Navarro |
| 7,221,733 B1 | 5/2007 | Takai |
| 7,233,688 B2 | 6/2007 | Ritt |
| 7,234,355 B2 | 6/2007 | Dewangan |
| 7,298,820 B2 | 11/2007 | Nelson |
| 7,339,159 B2 | 3/2008 | Juh |
| 7,349,523 B2 | 3/2008 | Jenkins |
| 7,352,840 B1 | 4/2008 | Nagarkar |
| 7,371,007 B2 | 5/2008 | Nilsson |
| 7,386,089 B2 | 6/2008 | Endo |
| 7,420,160 B2 | 9/2008 | Delaperriere |
| 7,453,976 B1 | 11/2008 | Yin |
| 7,471,765 B2 | 12/2008 | Jaffray |
| 7,515,681 B2 | 4/2009 | Ebstein |
| 7,579,608 B2 | 8/2009 | Takahashi |
| 7,605,365 B2 | 10/2009 | Chen |
| 7,668,292 B1 | 2/2010 | Bose |
| 7,734,010 B2 | 6/2010 | Otto |
| 7,750,311 B2 | 7/2010 | Daghighian |
| 7,766,903 B2 | 8/2010 | Blumenkranz |
| 7,773,723 B2 | 8/2010 | Nord |
| 7,778,383 B2 | 8/2010 | Koehler |
| 7,778,392 B1 | 8/2010 | Berman |
| 7,778,680 B2 | 8/2010 | Goode, Jr. |
| 7,782,998 B2 | 8/2010 | Langan |
| 7,945,022 B2 | 5/2011 | Nelms |
| 8,044,359 B2 | 10/2011 | Simon |
| 8,093,549 B2 | 1/2012 | Navarro |
| 8,130,905 B1 | 3/2012 | Nelms |
| 8,136,773 B2 | 3/2012 | Schmutzer |
| 8,147,139 B2 | 4/2012 | Papaioannou |
| 8,218,718 B1 | 7/2012 | Van Herk |
| 8,235,530 B2 | 8/2012 | Maad |
| 8,242,458 B2 | 8/2012 | Rinecker |
| 8,321,179 B2 | 11/2012 | Simon |
| 8,325,878 B2 | 12/2012 | McNutt |
| 8,430,564 B2 | 4/2013 | Simmons |
| 8,457,713 B2 | 6/2013 | Kagermeier |
| 8,474,794 B2 | 7/2013 | Liljedahl |
| 8,536,547 B2 | 9/2013 | Maurer |
| 8,541,756 B1 | 9/2013 | Treas |
| 8,605,857 B1 | 12/2013 | Renner |
| 8,632,448 B1 | 1/2014 | Schulte |
| 8,726,814 B1 | 5/2014 | Matteo |
| 8,794,899 B2 | 8/2014 | Cozza |
| 8,833,709 B2 | 9/2014 | Weng |
| 8,840,304 B2 | 9/2014 | Perez |
| 8,840,340 B2 | 9/2014 | Eisenhower |
| 8,874,385 B2 | 10/2014 | Takayanagi |
| 8,927,921 B1 | 1/2015 | Nelms |
| 9,050,460 B2 | 6/2015 | Hildreth |
| 9,097,384 B1 | 8/2015 | Simon |
| 9,463,336 B2 | 10/2016 | Nelms |

(56) References Cited

U.S. PATENT DOCUMENTS

| | | | |
|---|---|---|---|
| 9,480,861 B2 | 11/2016 | Kapatoes | |
| 9,561,388 B2 | 2/2017 | Hildreth | |
| 9,586,060 B2 | 3/2017 | Seuntjens | |
| 9,750,955 B2 | 9/2017 | McNutt | |
| 9,895,557 B2 | 2/2018 | Seuntjens | |
| 2001/0042841 A1 | 11/2001 | Lyons | |
| 2002/0077545 A1 | 6/2002 | Takahashi | |
| 2002/0080912 A1 | 6/2002 | Mackie | |
| 2003/0043879 A1 | 3/2003 | Tanaka | |
| 2003/0043960 A1 | 3/2003 | Op De Beek | |
| 2003/0138077 A1 | 7/2003 | Lee | |
| 2003/0231740 A1 | 12/2003 | Paliwal | |
| 2004/0066880 A1 | 4/2004 | Oikawa | |
| 2004/0068182 A1 | 4/2004 | Misra | |
| 2004/0096033 A1 | 5/2004 | Seppi | |
| 2004/0113094 A1 | 6/2004 | Lyons | |
| 2004/0120560 A1 | 6/2004 | Robar | |
| 2004/0211917 A1 | 10/2004 | Adamovics | |
| 2004/0228435 A1 | 11/2004 | Russell | |
| 2004/0251419 A1 | 12/2004 | Nelson | |
| 2005/0013406 A1 | 1/2005 | Dyk | |
| 2005/0077459 A1 | 4/2005 | Engler | |
| 2005/0111621 A1 | 5/2005 | Riker | |
| 2006/0002519 A1 | 1/2006 | Jenkins | |
| 2006/0033044 A1 | 2/2006 | Gentry | |
| 2006/0184124 A1 | 8/2006 | Cowan | |
| 2006/0203964 A1 | 9/2006 | Nyholm | |
| 2006/0203967 A1 | 9/2006 | Nilsson | |
| 2006/0266951 A1 | 11/2006 | Fritsch | |
| 2007/0041497 A1 | 2/2007 | Schnarr | |
| 2007/0041499 A1 | 2/2007 | Lu | |
| 2007/0071169 A1 | 3/2007 | Yeo | |
| 2007/0081629 A1 | 4/2007 | Yin | |
| 2007/0086577 A1 | 4/2007 | Kobayashi | |
| 2007/0195930 A1 | 8/2007 | Kapatoes | |
| 2008/0031406 A1 | 2/2008 | Yan | |
| 2008/0049896 A1 | 2/2008 | Kuduvalli | |
| 2008/0049898 A1 | 2/2008 | Romesberg, III | |
| 2008/0091388 A1 | 4/2008 | Failla | |
| 2008/0103834 A1 | 5/2008 | Reiner | |
| 2008/0118137 A1 | 5/2008 | Chen | |
| 2008/0260368 A1 | 10/2008 | Chang | |
| 2008/0292055 A1 | 11/2008 | Boone | |
| 2009/0003512 A1 | 1/2009 | Pouliot | |
| 2009/0067576 A1 | 3/2009 | Maltz | |
| 2009/0090870 A1 | 4/2009 | Ahnesjo | |
| 2009/0175418 A1 | 7/2009 | Sakurai | |
| 2009/0217999 A1 | 9/2009 | Becker | |
| 2009/0227841 A1 | 9/2009 | Miyako | |
| 2009/0250618 A1 | 10/2009 | Simon | |
| 2009/0252292 A1 | 10/2009 | Simon | |
| 2010/0008467 A1* | 1/2010 | Dussault | A61N 5/103 378/65 |
| 2011/0022360 A1 | 1/2011 | Simon | |
| 2011/0051893 A1 | 3/2011 | McNutt | |
| 2011/0085716 A1 | 4/2011 | Chefd Hotel | |
| 2011/0096906 A1 | 4/2011 | Langeveld | |
| 2011/0158386 A1 | 6/2011 | Payne | |
| 2011/0210258 A1 | 9/2011 | Black | |
| 2011/0248188 A1 | 10/2011 | Brusasco | |
| 2011/0278444 A1 | 11/2011 | Navarro | |
| 2011/0306864 A1 | 12/2011 | Zarate | |
| 2012/0014618 A1 | 1/2012 | Sun | |
| 2012/0025105 A1 | 2/2012 | Brown | |
| 2012/0292517 A1 | 11/2012 | Izaguirre | |
| 2012/0305793 A1 | 12/2012 | Schiefer | |
| 2012/0326057 A1 | 12/2012 | Remeijer | |
| 2013/0048883 A1 | 2/2013 | Simon | |
| 2013/0303902 A1 | 11/2013 | Smith | |
| 2014/0073834 A1 | 3/2014 | Hildreth | |
| 2014/0094642 A1 | 4/2014 | Fuji | |
| 2014/0105355 A1 | 4/2014 | Toimela | |
| 2014/0263990 A1 | 9/2014 | Kawrykow | |
| 2015/0080634 A1 | 3/2015 | Huber | |
| 2015/0087879 A1 | 3/2015 | Nelms | |
| 2015/0124930 A1 | 5/2015 | Verhaegen | |
| 2015/0238778 A1 | 8/2015 | Hildreth | |
| 2015/0283403 A1 | 10/2015 | Kapatoes | |
| 2015/0309193 A1 | 10/2015 | Kozelka | |
| 2016/0067479 A1 | 3/2016 | Marcovecchio | |
| 2016/0166857 A1 | 6/2016 | Nelms | |
| 2016/0310762 A1 | 10/2016 | Ramezanzadeh Moghadam | |
| 2017/0021194 A1 | 1/2017 | Nelms | |
| 2017/0274225 A1* | 9/2017 | Baecklund | A61N 5/1082 |
| 2018/0185672 A1 | 7/2018 | Ramezanzadeh Moghadam | |

FOREIGN PATENT DOCUMENTS

| | | |
|---|---|---|
| EP | 1060726 | 12/2000 |
| EP | 1060726 B1 | 6/2004 |
| EP | 2016445 | 1/2009 |
| EP | 2078537 A1 | 7/2009 |
| EP | 2117649 A2 | 11/2009 |
| EP | 2186542 | 5/2010 |
| EP | 2457237 | 5/2012 |
| EP | 2708919 A2 | 3/2014 |
| EP | 2865417 | 4/2015 |
| EP | 2904974 | 8/2015 |
| EP | 3074088 | 10/2016 |
| EP | 3075417 | 10/2016 |
| JP | 05154209 | 6/1993 |
| JP | 2003310590 A | 11/2003 |
| JP | 2008105882 | 5/2008 |
| JP | 2010215428 | 9/2010 |
| JP | 2010234521 | 10/2010 |
| WO | 1996001790 | 10/1996 |
| WO | 1997048990 | 12/1997 |
| WO | 1998013708 | 4/1998 |
| WO | 1998015851 | 4/1998 |
| WO | 1999009436 | 2/1999 |
| WO | 1999048044 | 9/1999 |
| WO | 2000010123 | 2/2000 |
| WO | 2006138513 | 12/2006 |
| WO | 2008013956 | 1/2008 |
| WO | 2009114669 | 9/2009 |
| WO | 2009120494 | 10/2009 |
| WO | 2009137794 | 11/2009 |
| WO | 2011011471 | 1/2011 |
| WO | 2012053440 | 4/2012 |
| WO | 2013049839 | 4/2013 |
| WO | 2013177677 | 12/2013 |
| WO | 2015024360 | 2/2015 |
| WO | 2015073899 | 5/2015 |
| WO | 2016172352 | 10/2016 |

OTHER PUBLICATIONS

Nelms, Benjamin et al.; "Evalution of a Fast Method of EPID-based Dosimetry for Intensity-modulated Radiation Therapy"; Journal of Applied Clinical Medical Physics, Jan. 1, 2010, pp. 140-157, XP055476020.

PCT App. No. PCT/US2018/020320; International Search Report and Written Opinion dated Jul. 24, 2018.

Office Action dated Sep. 12, 2018 for U.S. Appl. No. 14/694,865 (pp. 1-7).

"Hi-Art,"; www.tomotherapy.com; TomoTherapy, Madison, WI; 2007; pp. 1-8.

"Rapid Arc"; Varian Medical Systems, Inc., Palo Alto, CA; www.varian.com; 2007; pp. 1-8.

"VMAT"; Elekta,Ltd., Crawley UK; Document No. 4513 3710770; Oct. 8, 2008.

"Waterphantom Dosimetry"; Medical Physics, vol. 3, May/Jun. 1976; pp. 189.

Ahnesjo et al. Phys. Med. Biol. 44, R99-R155 1999.

Ahnesjo et al., Acta. Oncol., 26, 49-56, 1987.

Ahnesjo, Med. Phys. 16, 577-92, 1989.

Albers et al., CRC HAndbook of Chemistry and Physics, 87th Ed., Edited by R.C. Weast (CRC, Cleveland, 1976. pp. F-11, D-171, E-6.

Almond et al. In "AAPM TG-51 Protocol for Clinical Reference Dosimetry of Hign Energy Photon and Electron Beams" (Med. Phys. VI, 26, pp. 1847-1870, 1999.

(56) References Cited

OTHER PUBLICATIONS

Amanatides et al., Eurographics '87, Conference Proceedings, 1987.
Aspen Aerogels, Pyrogel.RTM. 2250 Datasheet (Aspen Aerogels, Inc., Northborough, 2010).
Benedick Fraass; "Quality Assurance for Clinical Radiotherapy Treatment Planning," Med Phys., 25(10), Oct. 1998; pp. 1773-1829.
Berlyand et al., "Portable Calorimeter for Measuring Absorbed Doses of X-Rays and Electrons from Accelerators", translated from Izeriternaya Teknika, No. 11, Nov. 1991, pp. 56-58.
Boutillon in "Gap Correction for the Calorimetric Measurement of Absorbed Dose in Graphite with a 60Co Beam" (Phys. Med. Biol., vol. 34, pp. 1809-1821, 1989.
Brusasco, C, et al. 'A Dosimetry System for Fast Measurement of 3D Depth-dose Profiles in Charged-particle Tumor Therapy with Scanning Techniques.' Nuclear Instruments & Methods in Physics Research, Section—B: Beam Interactions With Materials and Atom 168.4 (2000): 578-92.
Cyberknife; Cyberknife Systems; "The Standard of Radiosurgery" by Accuracy, Sunnyvale, CA; 2009; pp. 1-6.
D.W.O. Rogers; "Montey Carlo Techniques in Radiotherapy,"; Physics in Canada, Medical Physics Special Issue, v. 58 #2; 2002; pp. 63-70.
Daures et al., "New Constant-Temperature Operating Mode for Graphite Calorimeter at LNE-LNHB", Physics in Medicine and Biology, vol. 50, 2005, No. pp. 4035-4052.
Daures et al., "Small section graphite calorimeter (CR10) at LNE-LNHB for measurement in small beams for IMRT", METROLOGICA, (Dec. 1, 2011), XP020229547.
Daures et al., "Small Section Graphite Calorimeter (GR-10) at LNE-LNHB for Measurements in Small Beams for IMRT Metrologia", vol. 49, No. 5, 2012, pp. S174-S178.
Domen et al., "A Heat-loss-Compensated Calori meter: Theory, Design, and Performance", Journal of Research of the National Bureau of Standards—A. Physics and Chemistry, vol. 78A, No. 5, Sep.-Oct. 1974, pp. 595-610.
Domen, "Absorbed Dose Water Calorimeter" (Med. Phys., vol. 7, pp. 157-159).
Duane et al., "An Absorbed Dose Calorimeter for IMRT Dosimetry", Metrologia, vol. 49, No. 5, 2012, pp. S168-S173.
EP2277353 Search Report dated Jul. 21, 2017.
EP2457237 Supplemental European Search Report and Written Opinion dated Mar. 8, 2017.
G.J. Kutcher; "Comprehensive AQ for Radiation Oncology Report;" AAPM Radiation Therapy Committee Task Group 40; Med. Phys., 21; Apr. 1994; pp. 581-618.
IAEA, TRS., "398. Absorbed Dose Determination in External Beam Radiotherapy: An International Code of Practice for Dosimetry based on Standards of Absorbed Dose to Water," Vienna International Atomic Energy Agency (2000).
Indra J. Das, Chee-Wai Cheng, Ronald J. Watt, Anders Ahnesjo, John Gibbons, X. Allen Li, Jessica Lowenstien, Raj K. Mitra, William E. Simon, Timothy C. Zhu; Accelerator Beam Data Commissioning Equiptment and Procedures; Report of the TG-106 of the Therapy Physics Committee of the AAPM; Med. Phys. 35(9), Sep. 2008; pp. 4186-4215.
J. Seuntjens and S. Duane, "Photon absorbed dose standards," Metrologia 46, S39-S58 (2009).
Joseph O. Deasy; "A Computational Environment for Radiotherapy Research," Med. Phys. 30, (5), May 2003; pp. 979-985.
Kawrakow et al. In "The EGSnrc Code System: Monte-Carlo Simulation of Electron and Photon Transport" (Canadian National Research Center, NRC Report PIRS-701, 2006.
Liu et al., Med. Phys. 24, 1729-1741, 1997.
Lu et al., Phys. Med. Biol. 50, 655-680, 2005.
Mackie et al., Med. Phys. 12, 188-196, 1985.
Mackie et al., Phys. Med. Biol. 33, 1-20, 1988.
Mackie et al., Use of Comp. In Rad. Ther., 107-110 1987.
MapCALC; www.sunnuclear.com; manufactured by Sun Nuclear Corp.; Melbourne, FL; 2009.

MapCheck and EPIDose; www.sunnuclear.com; manufactured by Sun Nuclear Corp.; Melbourne,FL; 2010.
Mathilda Van Zijtveld, Maaretn L.P. Dirkxa, Hans C.J. De Boera, and Ben J.M. Heijmen; "3D Dose Reconstruction for Clinical Evaluation of IMRT Pretreatment Verification with an EPID." Radiotherapy and Oncology, 82(2); Feb. 2007; pp. 201-201.
Mc Ewen at al., 'A Portable Calorimeter for Measuring Absorbed Dose in the Radiotherapy Clinic', Physics in Medicine and Biology, vol. 45, No. 12, Dec. 2000, pp. 3675-3691.
McDonald et al., "Portable Tissue Equivalent Calorimeter", Medical Physics, vol. 3, 2, Mar.-Apr. 1976, pp. 80-86.
McEwen et al., Portable Graphite Calorimeter for Measuring Absorbed Dose in the Radiotherapy Clinic.Standards and Codes of Practice in Medical Radiation Dosimetry,IAEA-CN-96-9P,2002, pp. 115-121.
Miller, "Polystyrene Calorimeter for Electron Beam Dose Measurements", Radiation Physics Chemistry vol. 46, No. 4-6, Aug. 1995, pp. 1243-1246.
Mohan et al., Med. Phys. 12, 592-597, 1985.
Myers et al., "Precision Adiabatic Gamma-Ray Calorimeter using Thermistor Thermometry", Review of Scientific Instruments, vol. 32, No. 9, Sep. 1961, pp. 1013-1015.
Nelms, Benjamin. "Variation in External Beam Treatment, Plan Quality: An Interinstitutional Study of Planners and Planning Systems." Practical Radiation Oncology 2.4 (2012): 296-305.
Nutbrown et. "Evaluation of Factors to Convert Absorbed Dose Calibrations in Graphite to Water for Mega-Voltage Photon Beams" (UK National Pysical Laboratory, NPL Report CIRM 37, 2000.
Ostrowsky et al., "The Construction of the Graphite Calorimeter GR9 at LNE-LNHB (Geometrical and technical considerations)", Report CEA-R-6184, 2008, 52 pages.
Otto, Med. Phys. 35, 310-317, 2008.
Owen et al "Correction for the Effect of the Gaps around the Core of an Absorbed Dose Graphite Calorimeter in High Energy Photon Radiation" (Phys. Med. Biol., vol. 36, pp. 1699-1704, 1991.
Palmans et al., "A Small-Body Portable Graphite Calorimeter for Dosimetry in Low-Energy Clinical Proton Beams", Physics in Medicine and Biology, vol. 49, No. 16, Aug. 2004, pp. 3737-3749.
Papanikolaou et al., Med. Phys. 20, 1327-1336, 1993.
PCT App. No. PCT/US2009/036775; International Preliminary Report on Patentability Chapter II and Written Opinion dated Sep. 12, 2010.
PCT App. No. PCT/US2009/036775; International Search Report dated Nov. 12, 2009.
PCT App. No. PCT/US2009/036917; International Preliminary Report on Chapter II Patentability dated Mar. 15, 2011.
PCT App. No. PCT/US2009/036917; International Search Report dated Sep. 17, 2009.
PCT App. No. PCT/US2009/036917; Written Opinion dated Sep. 12, 2010.
PCT App. No. PCT/US2009/043341; International Preliminary Report on Patentability Chapter I dated Nov. 9, 2010.
PCT App. No. PCT/US2009/043341; International Search Report dated Jan. 5, 2010.
PCT App. No. PCT/US2009/043341; Written Opinion of the International Search Authority dated Nov. 8, 2010.
PCT App. No. PCT/US2010/042680; International Preliminary Report on Patentability Chapter I dated Jan. 24, 2012.
PCT App. No. PCT/US2010/042680; International Search Report dated Jan. 27, 2011.
PCT App. No. PCT/US2010/042680; International Written Opinion dated Jan. 23, 2012.
PCT App. No. PCT/US2012/053440; International Preliminary Report on Patentability Chapter I dated Mar. 3, 2015.
PCT App. No. PCT/US2012/053440; International Search Report and Written Opinion dated Mar. 26, 2014.
PCT App. No. PCT/US2012/058345; International Preliminary Report on Patentability Chapter I dated Apr. 1, 2014.
PCT App. No. PCT/US2012/058345; International Search Report dated Apr. 17, 2013.
PCT App. No. PCT/US2012/058345; International Written Opinion of the International Search Authority dated Mar. 29, 2014.
PCT App. No. PCT/US2014/065808; International Preliminary Report on Patentability Chapter I dated May 17, 2016.

(56) References Cited

OTHER PUBLICATIONS

PCT App. No. PCT/US2014/065808; International Search Report and Written Opinion dated May 21, 2015.
PCT App. No. PCT/US2015/024360; International Preliminary Report on Patentability Chapter I dated Oct. 4, 2016.
PCT App. No. PCT/US2015/024360; International Search Report and Written Opinion dated Oct. 8, 2015.
PCT App. No. PCT/US2016/028664; International Preliminary Report on Patentability dated Nov. 2, 2017.
PCT/US2017/044472; International Search Report and Written Opinion of the International Searching Authority, or the Declaration dated Oct. 13, 2017.
Petree et al., "A Comparison of Absorbed Dose Determinations in Graphite by Cavity Ionization Measurements and by Calorimetry", Journal of Research of the National Bureau of Standards—C. Engineering and Instrumentation. vol. 71 C, No. 1, Jan.-Mar. 1967, pp. 19-27.
Picard et al., "Construction of an Absorbed-Dose Graphite Calorimeter", Report BIPM-09/01' May 2009, 12 pages.
R. Alfonso et al., 'A new formalism for reference dosimetry of small and nonstandard fields,' Med. Phys. 35, 5179-5186 (2008).
Renaud et al., "Development of a graphite probe calorimeter for absolute clinical dosimetry", Med. Phvs., (20130109), vol. 40, No. 2, p. 020701, XP012170941.
Robert M. Eisberg; "Fundamentals of Modern Physics," Chapter 9—Perturbation Theory; John Wiley & Sons; 1967; pp. 268-272.
Rogers, "The physics of AAPM's TG-51 protocol," in Clinical Dosimetry Measurements in Radiotherapy, Medical Physics Monograph No. 34, edited by D. W. O. Rogers and J. E. Cygler (Medical Physics Publishing, Madison, WI, 2009), pp. 239-298.
Ross et al. In "Water Calorimetry for Radiation Dosimetry" (Phys. Med. Biol., vol. 41, pp. 1-29).
S. Picard, D. T. Burns, and P. Roger, "Determination of the specific heat capacity of a graphite sample using absolute and differential methods," Metrologia 44, 294-302 (2007).
Sander et al., "NPL's new absorbed dose standard for the calibration of HDR 192Ir brachytherapy sources," Metrologia 49, S184-S188 (2012).
Seuntjens et al., Review of Calorimeter Based Absorbed Dose to Water Standards, Standards and Codes of Practice in Medical Radiation Dosimetry, IAEA-CN-96-3,2002 p. 37-66.
Stewart in "The Development of New Devices for Accurate Radiation Dose Measurement: A garded Liquid Ionization Chamber and an Electron Sealed Water Calorimeter" (Ph. D. Dissertation McGill University, 2007.
Sundara et al., "Graphite Calorimeter in Water and Calibration of Ionization Chambers in Dose to Water for 60Co Gamma Radiation", Medical Physics, vol. 7, No. 3, May-Jun. 1980, pp. 196-201.
T.R. McNutt, T.R. Mackie, P.J. Reckwerdt, B.R. Paliwal; "Analysis and Convergence of the Iterative Convolution/Superposition Dose Reconstruction Technique,"; Med. Phys. 24(9) Sep. 1997; pp. 1465-1476.
Williams, SIGGRAPH Comput. Graph. 17, 3, 1-11, 1983.
Witzani et al., "A Graphite Absorbed-Dose Calorimeter in the Quasi-Isothermal Mode of Operation", Metrologia, vol. 20, No. 3, 1984, pp. 73-79.
Y. Morishita et al., "A standard for absorbed dose rate to water in a 60Co field using a graphite calorimeter at the national metrology institute of Japan," Radiat. Prot. Dosim. 1-9 (2012) (published E-first Sep. 5, 2012).
Yan et al., Phys. Med. Biol. 42, 123-132, 1997.
Yu, Phys. Med. Biol. 40, 1435-1449, 1995.
PCT App. No. PCT/US2017/062608; International Search Report and Written Opinion dated Feb. 22, 2018.
McEwen et al.; A portable calorimeter for measuring absorbed dose in radiotherapy clinic; Dec. 2000; Phys. Med. Biol., vol. 45; pp. 3675-3691.
Linacre, J.K., "Harwell Graphite Calorimeter", IAEA, vol. 47, 1970 (pp. 46-54.).
Office Action dated Dec. 28, 2018 for U.S. Appl. No. 15/932,363 (pp. 1-11).
Office Action dated Feb. 7, 2019 for U.S. Appl. No. 15/395,852 (pp. 1-14).
Crossfield, Mike, "Have null, will fly." IEE Review (vol. 47, Issue 1), Jan. 2001 (pp. 31-34).
Karsten, R. P., "The Use of Flying Null Technology in the Tracking of Labware in Laboratory Automation," JALA: Journal of the Association for Laboratory Automation, 2001, 6(5), (pp. 67-70).
Sparavigna, Amelia, "Labels discover physics: the development of new labelling methods as a promising research field for applied physics," 2008, (pp. 1-16).
Office Action dated Mar. 26, 2019 for U.S. Appl. No. 14/694,865 (pp. 1-6).
Notice of Allowance dated May 6, 2019 for U.S. Appl. No. 15/932,363 (pp. 1-5).

* cited by examiner

0 Radian Orientation

π Radian Orientation

0 Radian Orientation

π Radian Orientation

BEAM ANGLE DIRECTION DETERMINATION

RELATED APPLICATION(S)

The current application claims priority under 35 U.S.C. § 119 to U.S. Provisional Patent Application No. 62/367,932 filed Jul. 28, 2016 and entitled "Beam Angle Direction Determination," the contents of which are hereby incorporated by reference in their entirety.

BACKGROUND

Radiation therapy is used to treat cancerous tumors with ionizing radiation that kills the affected cancer cells. External beam radiotherapy can be used to deliver ionizing radiation. In such therapy, a patient is placed on a couch and a radiotherapy beam generator is positioned to direct the ionizing radiation at the patient's tumor.

A linear accelerator ("LINAC") is typically used for the purpose of delivering external beam radiation treatments to patients. A LINAC can deliver high-energy x-ray beams to the region of the target tissue, where the x-ray is sufficiently focused to destroy the target cells (e.g., tumor cells, abnormal cells, etc.), while avoiding the surrounding normal tissue.

SUMMARY

A system is disclosed that includes a radiation therapy device with a gantry. The radiation therapy device is configured to deliver a radiation beam at an angle determined by orientation of the gantry. Also, a pair of radiation detectors are located at a fixed position to receive radiation originating from the radiation beam. Each of the radiation detectors in the pair generate differing responses to the radiation beam at the angle. The system further includes computer hardware configured to perform operations that determine the angle of the gantry utilizing the differing responses from the pair of radiation detectors.

In some variations one or more of the following features can optionally be included in any feasible combination. The computer hardware can be further configured to display the determined angle, to compare the determined angle to a planned angle, or to use the determined angle in a dose calculation.

In other variations, the fixed position of the pair of radiation detectors can be within the radiation beam. The fixed position of the pair of radiation detectors can be outside of the radiation beam and the pair of radiation detectors can detect scattered radiation. The pair of radiation detectors can be mounted on a single substrate or on different substrates. The radiation detectors in the pair can be oriented in opposite directions. The radiation detectors can generate differing responses due to their orientation, due to the detectors being of different types, or due to the placement of radiation absorbing material.

In yet other variations, the detectors can be close together or have a separation between the pair of radiation detectors of approximately 2.5 mm.

In some variations, the system can include multiple pairs of radiation detectors, and the determining can be based on the differing responses of multiple close together pairs of radiation detectors. The system can also include a flat array of radiation detectors including the pair of radiation detectors.

In an interrelated aspect, a system is disclosed that includes a pair of radiation detectors located at a fixed position to receive radiation originating from a radiation therapy device configured to deliver a radiation beam at an angle determined by orientation of a gantry. Each of the radiation detectors in the pair generate differing responses to the radiation beam at the angle. Computer hardware is configured to perform operations that include determining the angle of the gantry utilizing the differing responses from the pair of radiation detectors.

In another interrelated aspect, a computer program product is disclosed that includes a non-transient, machine-readable medium storing instructions which, when executed by at least one programmable processor, cause the at least one programmable processor to perform operations that include receiving detector data from a pair of radiation detectors located at a fixed position to receive radiation originating from a radiation therapy device configured to deliver a radiation beam at an angle determined by orientation of a gantry. Each of the radiation detectors in the pair generate the detector data based at least on differing responses to the radiation beam at the angle. The operations also include determining the angle of the gantry utilizing the differing responses from the pair of radiation detectors and calculating a dose based at least on the determined angle.

Implementations of the current subject matter can include, but are not limited to, methods consistent with the descriptions provided herein as well as articles that comprise a tangibly embodied machine-readable medium operable to cause one or more machines (e.g., computers, etc.) to result in operations implementing one or more of the described features. Similarly, computer systems are also contemplated that may include one or more processors and one or more memories coupled to the one or more processors. A memory, which can include a computer-readable storage medium, may include, encode, store, or the like, one or more programs that cause one or more processors to perform one or more of the operations described herein. Computer implemented methods consistent with one or more implementations of the current subject matter can be implemented by one or more data processors residing in a single computing system or across multiple computing systems. Such multiple computing systems can be connected and can exchange data and/or commands or other instructions or the like via one or more connections, including but not limited to a connection over a network (e.g., the internet, a wireless wide area network, a local area network, a wide area network, a wired network, or the like), via a direct connection between one or more of the multiple computing systems, etc.

The details of one or more variations of the subject matter described herein are set forth in the accompanying drawings and the description below. Other features and advantages of the subject matter described herein will be apparent from the description and drawings, and from the claims. While certain features of the currently disclosed subject matter are described for illustrative purposes in relation to particular implementations, it should be readily understood that such features are not intended to be limiting. The claims that follow this disclosure are intended to define the scope of the protected subject matter.

BRIEF DESCRIPTION OF THE DRAWINGS

The accompanying drawings, which are incorporated in and constitute a part of this specification, show certain aspects of the subject matter disclosed herein and, together with the description, help explain some of the principles associated with the disclosed implementations. In the drawings.

DETAILED DESCRIPTION

During radiation therapy, a patient can be positioned on a patient couch and a radiation beam can be delivered to a target tissue of patient. The target tissue can be previously identified through use of various scanning technologies such as magnetic resonance imaging or computed tomography. The positioning of the patient can also be predetermined so that the location of the delivery of the radiation beam is accurate.

To deliver a proper radiation treatment to a patient, a radiation treatment plan can be developed. The plan can include, for example, information about radiation delivery, delivery log information, time, dose information, treatment beam shape or energy, orientation or angle of the gantry, collimator leaf positions, patient anatomy orientation with respect to the treatment beam (e.g., CT images), any other measurements, and/or any other data.

One of the attributes of clinical radiotherapy ("RT") is an ability to change the LINAC's gantry angle over the course of a treatment fraction. The fraction can include one or more (e.g., seven) fields of radiation. The gantry angle can be used to determine the radiation beam entrance angle to the patient, to ensure that treatment of target tissue (e.g., tumor, abnormal, etc.) takes places at an intersection of the fields delivered during the fraction, while healthy tissue is substantially unaffected. A fraction can be characterized by stationary angles (e.g., blocked fields or intensity-modulated radiation therapy ("IMRT")) and/or continuously changing gantry angles while the field shape is modulated to conform to the target volume (after referred to as volumetric arc therapy ("VMAT")).

Figure 1:
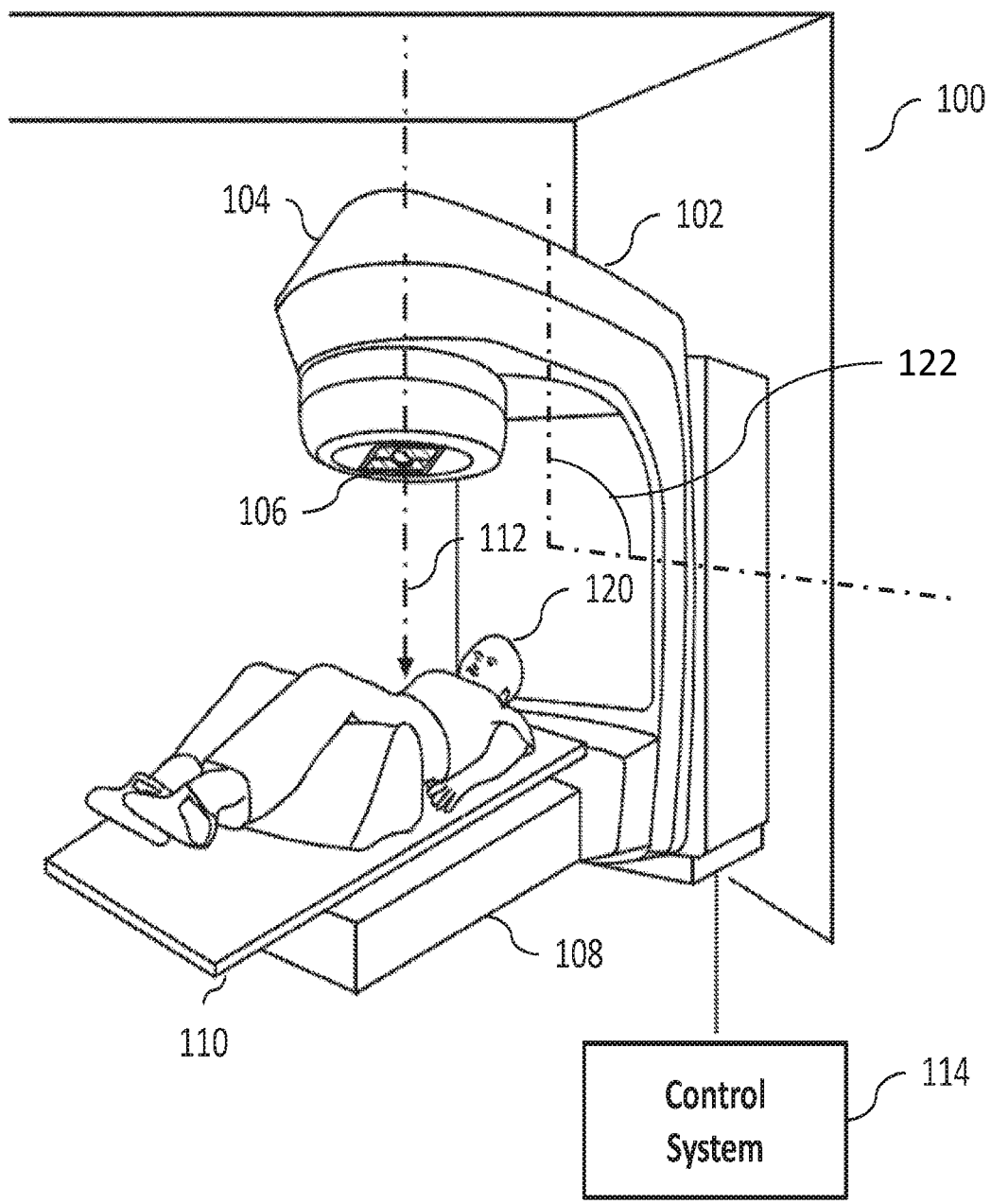
FIG. 1 is a simplified diagram illustrating a radiation therapy system, according to some implementations of the current subject matter.

FIG. 1 illustrates an exemplary radiation system 100 according to some implementations of the current subject matter. Radiation system 100 can include radiation therapy device 102, gantry 104, beam collimator 106, radiation detector (or a radiation detector array) 108, patient couch 110, and control system 114.

The gantry 104 can include radiation therapy device 102 that can have a radiation source such as a LINAC, Cobalt 60 source, etc., that can direct radiation toward patient 120 by way of radiation beam 112. Radiation beam 112 can include scanning beams, where a small beamlet can be scanned over the area that is required to be treated. Radiation beam 112 may also be shaped by beam collimator 106 prior to application to patient 120. Though radiation beam 112 is illustrated as a line in FIG. 1, it is understood that this is only a simplification and that radiation beam 112 has a two dimensional cross-section. The cross-section can be determined at least by shaping with beam collimator 106.

In some implementations, gantry 104 can rotate about patient 120. The angle of the gantry 104 (and radiation beam 112) is shown in FIG. 1 as gantry angle 122. Gantry 104 can rotate 360° around patient 120, or have a more limited range of rotation. It is contemplated that gantry 104 can rotate to any desired angle as specified by an operator, a radiation treatment plan, control system 114, or the like, within the limits of radiation system 100. The above exemplary rotation ranges and the simplified illustration of gantry angle 122 in FIG. 1 are not intended to be limiting except as explicitly described herein.

Operation of radiation system 100 can be controlled using control system 114, which can include processors, computers, hardware, computer programs, and any combination thereof. Control system 114 can be used to determine how radiation beam 112 can be delivered to the patient, the rotation of gantry 104, the positioning of patient 120, as well as other parameters of the treatment process. Control system 114 can also be used to monitor patient 120 during the treatment (e.g., a treatment fraction) and/or change treatment parameters, if so required. Control system 114 may be used to perform quality assurance ("QA") to ensure that accurate radiation treatment is delivered. Radiation system 100 can be designed to deliver radiation therapy to any part of the human body, where only a portion of the human body can be placed in the vicinity of the radiation system 100.

Radiation therapy device 102 can be periodically tested to verify its ability to deliver radiation fields defined by a standardized QA protocol, as well as its ability to deliver radiation fields defined by a treatment planning system ("TPS") for a specific patient treatment. As shown in FIG. 1, radiation system 100 can include radiation therapy device 102 with gantry 104. Radiation therapy device 102 can be configured to deliver radiation beam 112 at an angle determined by orientation of gantry 104. As part of the radiation system QA, gantry angle 122 can be verified to ensure accurate radiation delivery.

According to certain aspects of the present disclosure, radiation detectors can be utilized to provide an independent measurement of gantry angle 122 by analyzing specific radiation detector responses due to received radiation. In some implementations, a pair of radiation detectors can be located at a fixed position to receive radiation originating from radiation beam 112. Radiation detector 108 can include one or more of pairs of radiation detectors, or, alternatively, an odd number of detectors. In one implementation, radiation detectors can be placed in the path of radiation beam 112, either before or after a patient 120. In another implementation, radiation detectors may be utilized in a quality assurance procedure prior to a treatment, for example, detectors may be placed within a phantom or directly within radiation beam 112 with no other materials.

As used herein, reference to the pair of radiation detectors being "within the radiation beam" is understood to mean that the radiation detectors directly receive the radiation beam, as opposed to only receiving scattered radiation. For example, the radiation detectors may be between patient 120 (or phantom) and radiation therapy device 102, or on the other side of patient 120 (or phantom) but still in a direct line with the beam of radiation therapy device 102.

In another implementation, the pair of radiation detectors can be outside of radiation beam 112 and detect scattered radiation. For example, the pair of radiation detectors can be a part of radiation detector 108 that is not directly in the path of radiation beam 112 or can be mounted elsewhere in the treatment room (e.g., on the walls, ceiling, etc.).

The pair of radiation detectors can be disposed anywhere that the direct radiation or the scattered radiation can be intercepted. In some implementations, the pair of radiation detectors can be close together such that adjacent radiation detectors effectively receive the same amount of radiation (neglecting any intervening materials). For example, adjacent radiation detectors (in the pair or otherwise) can be in contact, or separated by 1 mm, 2 mm, 2.5 mm, less than a centimeter, 1-5 cm, etc. The separation between adjacent radiation detectors can be based in part on the radiation field size either at the patient, at the phantom, or at the detector location. In some implementations, the separation can be proportional to the smallest field size dictated by the radiation treatment plan. In implementations of the current subject matter where multiple pairs of radiation detectors are utilized in the determination of gantry angle 122, the multiple pairs may be similarly configured to be close together.

In other implementations, the pair of radiation detectors can be part of an array or multiple pairs of radiation detectors. Determination of the gantry angle 122 can be based on one or more close pairs of radiation detectors.

In other implementations, there can be a flat array of radiation detectors that include the pair of radiation detectors. The flat array can be mounted at the radiation detector 108, on the walls, ceiling, etc.

As used herein, the term "response" refers to a raw or processed output of the pair of radiation detectors (or of radiation detector 108) that is generated when radiation is intercepted by the detector. For example a response can be an electrical signal generated by each detector of the pair of radiation detectors, or a scaled/normalized/processed representation of such. Also as used herein, the term "signal" refers to a raw detector output, for example a voltage, current, etc.

Each of the radiation detectors in the pair can be configured to generate differing responses to the radiation beam depending on the angle of gantry 104. For example, because of the angular sensitivity of certain detectors, if they are oriented differently, the radiation intercepted by one radiation detector can generate a first response at a particular gantry angle 122 and the radiation intercepted by the other detector in the pair can generate a second (and different) response. The difference in (or alternatively the ratio of) the two responses can then be a function of gantry angle 122. When gantry angle 122 changes, the differing responses (or response ratio) can change accordingly. Conversely, if the radiation emitted from radiation therapy device 102 changes due to, for example, only a change in the beam output due to the opening or closing of beam collimator 106 or a change in the beam energy, then the difference in responses can remain unchanged because gantry angle 122 has not changed.

With a calibrated pair of radiation detectors, gantry angle 122 can be calculated. To calibrate the pair of radiation detectors, gantry 104 can be rotated to different gantry angles and the response of the pair of radiation detectors can be measured at each gantry angle 122. The calibration can be stored as a data file on a connected computing system and accessed as part of a QA process or as part of radiation treatment delivery.

A pair of radiation detectors can generate differing responses for different reasons, depending on various implementations of the present disclosure. For example, the differing responses can be due to their orientation, due to the pair of radiation detectors being of different types, or due to the placement of radiation absorbing material. When the response of a single radiation detector is a function of angle (e.g., the radiation detector generates a stronger signal when the radiation strikes it head-on as opposed to striking from the side or the rear), the differing responses (to radiation striking the pair of radiation detectors at the same angle) can be due to the radiation detectors in the pair being oriented in different directions or opposite directions. Examples of such orientations are shown in FIGS. 2A, 2B, 3A, and 3B. In other implementations, when the radiation detectors are different types of radiation detectors, they can have a different response as a function of incident radiation angle even if they are mounted in the same orientation. For example, a first type of radiation detector can have a factor of two increase in signal when gantry angle 122 changes from 0 to 30° and a second type of radiation detector can have a factor of three increase for the same change in gantry angle 122. For each type of radiation detector, a known response as a function of incident radiation angle can allow gantry angle 122 to be determined. In yet another implementation, intervening material (e.g., radiation absorbing or scattering material such as lead) can also provide a difference in response between the pair of radiation detectors.

Computer hardware can be configured to perform operations that determine gantry angle 122 utilizing the differing responses from the pair of radiation detectors. This can include each of the radiation detectors in the pair generating detector data based at least on differing responses to the radiation beam at gantry angle 122. The computer hardware can also calculate a delivered dose based partially on the determined angle. Also, once gantry angle 122 is determined by any of the implementations described herein, the computer hardware can display the determined gantry angle 122, can compare the determined angle to a planned angle, or can use the determined angle in a dose calculation. In some implementations, the system responsible for determining gantry angle 122 can include the pair of radiation detectors and the computer hardware separate from the radiation therapy device 102.

In some implementations, the QA device can include one or more lines of detectors and/or an array of detectors that can be used to determine gantry angle 122. The array of radiation detectors can include any number of pairs of radiation detectors. As discussed above with reference to a single pair of radiation detectors, in some exemplary implementations, line(s) or planar array(s) of detectors in a QA device can have a significant directional response due to their asymmetric construction. In some implementations, the current subject matter provides for a two-dimensional planar array of detectors that can be used to account for the directional response of detectors. The two-dimensional planar array of detectors can enable determination of gantry beam angle based on its own radiation measurement data. While the present disclosure describes embodiments utilizing pair(s) of detectors, it is contemplated that other groupings of detectors greater than one may be similarly utilized to determine gantry angle 122.

Figure 2A:
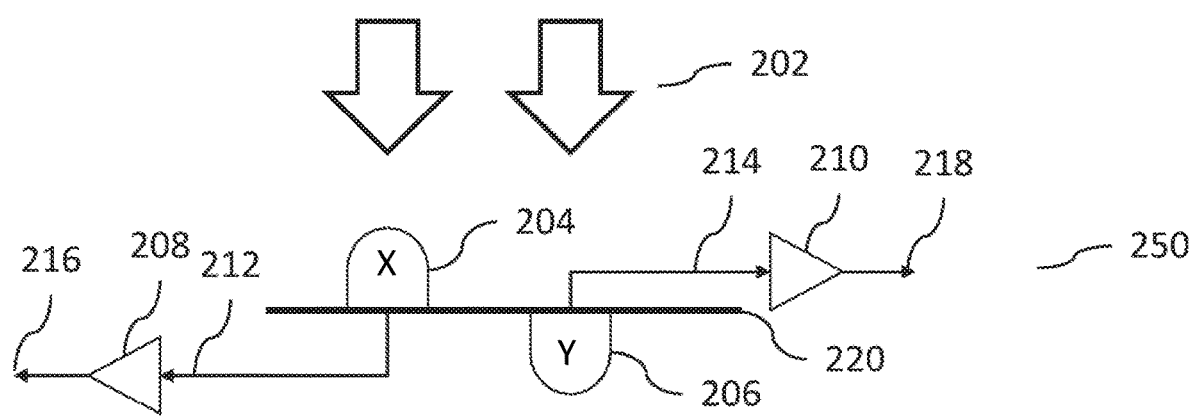
FIG. 2A illustrates an exemplary pair of radiation detectors at a 0 radian orientation, according to some implementations of the current subject matter.
Figure 2B:
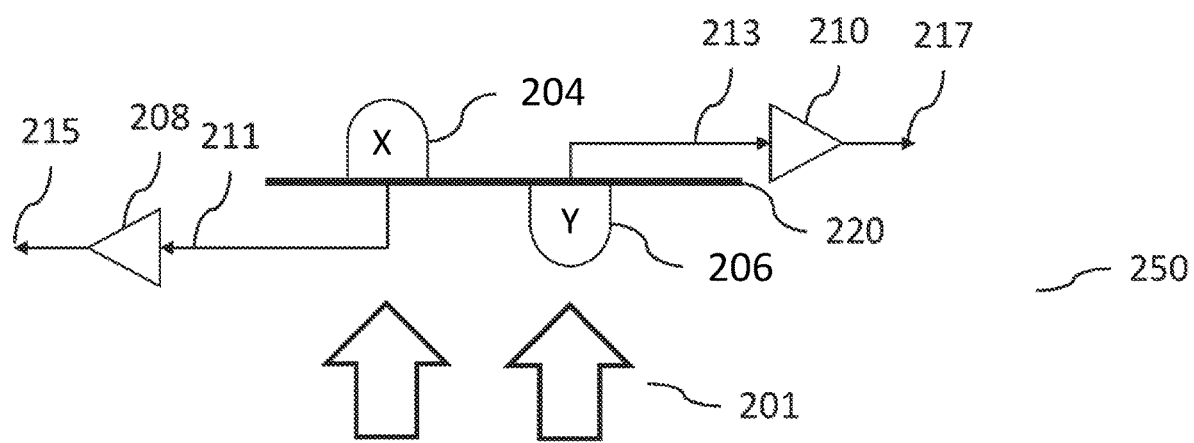
FIG. 2B illustrates the exemplary pair of radiation detectors from FIG. 2A at a π radian orientation, according to some implementations of the current subject matter.
Figure 3A:
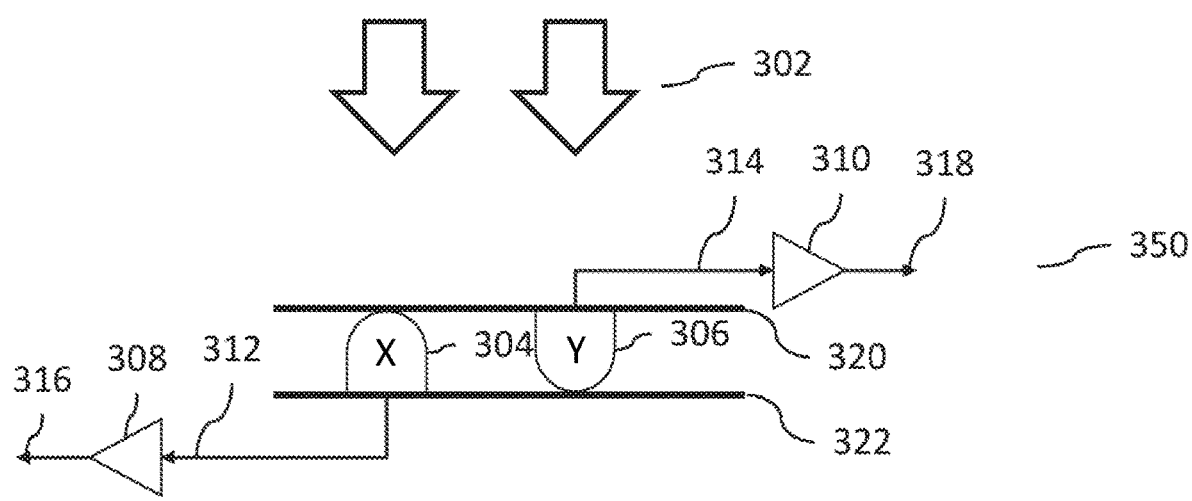
FIG. 3A illustrates an alternative implementation of an exemplary pair of radiation detectors at a 0 radian orientation, according to some implementations of the current subject matter.
Figure 3B:
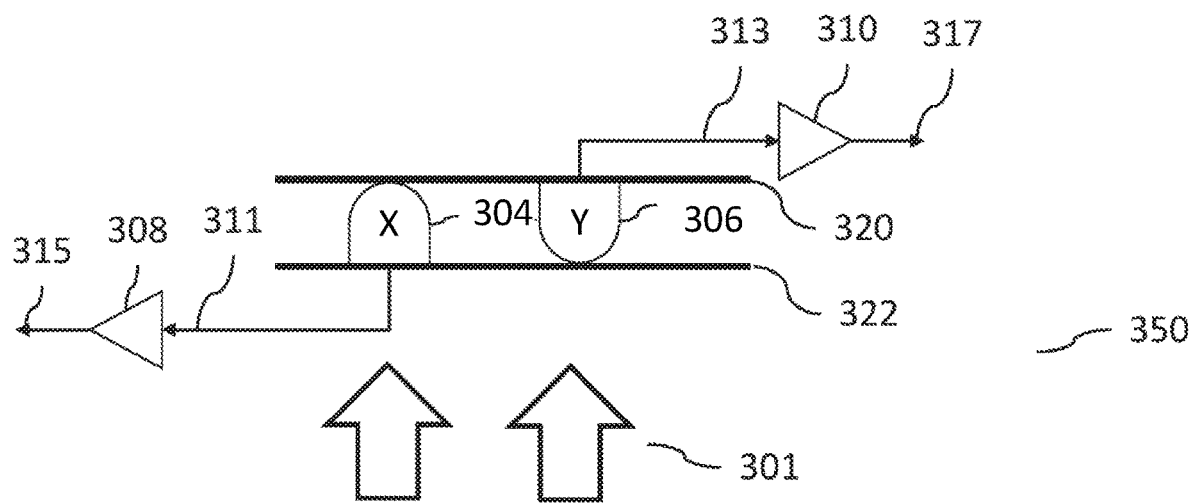
FIG. 3B illustrates an alternative implementation of the exemplary pair of radiation detectors from FIG. 3A at a π radian orientation, according to some implementations of the current subject matter.

FIG. 2A illustrates an exemplary pair of radiation detectors at a 0 radian orientation, according to one implementation of the current subject matter. FIG. 2B illustrates the exemplary pair of radiation detectors from FIG. 2A at a π radian orientation, according to one implementation of the current subject matter. FIG. 3A illustrates an alternative implementation of an exemplary pair of radiation detectors at a 0 radian orientation. FIG. 3B illustrates an alternative implementation of the exemplary pair of radiation detectors from FIG. 3A at a π radian orientation.

An array of detectors consistent with implementations of the present disclosure may be utilized with any radiation delivery system, including but not limited to, radiation system 100 shown in FIG. 1. As shown in FIGS. 2A, 2B, 3A, and 3B, (showing only a single pair of radiation detectors, which may be included in an array 250) the radiation detectors can be mounted in odd and/or even orientations. As used herein, reference to "odd" and "even" is an arbitrary label that is intended to merely distinguish between different orientations of the pairs of detectors relative to incident radiation. For example, an "even" orientation refers to a radiation detector oriented to receive radiation head-on or in an approximately 180 degree arc "in front" of the detector. In contrast, an "odd" orientation refers to a radiation detector oriented to receive radiation predominantly from the other side (or "rear") of the radiation detector.

Figure 4:
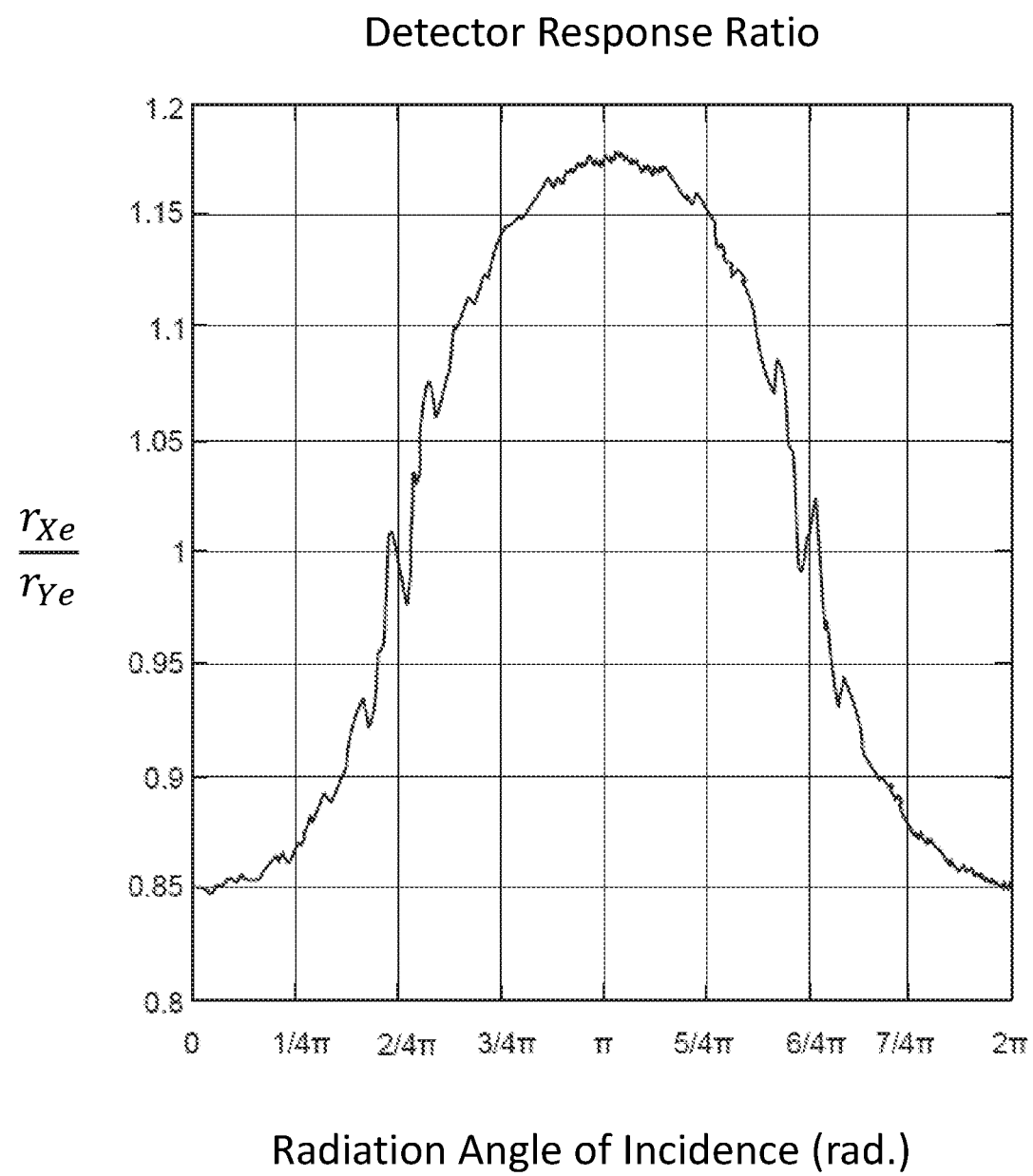
FIG. 4 illustrates an exemplary experimental detector response ratio plot as a function of gantry angle, according some implementations of the current subject matter.

The detectors can generate specific responses to radiation that is incident upon the detectors. The responses can be different based on the direction of the radiation, which can include, for example, incidence angles of 0 and/or π radians as shown in the figures. The differences between responses can be measured using known angles of incidence, which can be determined using a calibrated inclinometer and/or any other means. Using the detectors' responses data, a response plot, being indicative of a ratio of radiation detector responses, can be generated (an exemplary response plot illustrating detector response ratios versus angles of incidence to a pair of detectors is shown in FIG. 4). Based on the response plot, a determination of a gantry angle 122, as the gantry rotates, can be made. Thus, using the exemplary detector array systems having odd-even orientations of detector(s), as shown in FIGS. 2A and 2B or 3A and 3B, an angle of incidence for a radiation detector can be determined based on the determined and/or known directional response of its neighbor detector, thereby allowing determination of a gantry angle 122. In some implementations, arrays 250 can be planar (or flat), where neighboring detectors can be oriented π radians with regard to one another (as shown in FIGS. 2A and 2B or 3A and 3B). Such arrays 250 can have a mathematical parity in detector orientation that can switch between odd and even orientations between neighboring detectors, with odd or even arbitrarily defined in accordance with orientation of the detector, as described above.

Referring to FIG. 2A, an exemplary array 250 can be arranged in a 0 radians orientation with respect to incident beam 201 (as opposed to the π radians orientation of the array shown in FIG. 2B). As can be understood, the arrangements shown in FIGS. 2A and 2B are for illustrative purposes only and are not intended to limit the current subject matter. The shown orientations can be based on an angle of incidence of a radiation beam. An array 250 can include a substrate (e.g., a printed circuit board ("PCB")) 220 that can be used to mount irradiating detectors 204 and 206, where detector 204 is mounted in an even orientation and detector 206 is mounted in an odd orientation with respect to the incident beam 202. Detectors 204, 206 can be communicatively coupled to measuring electronics 208, 210, respectively. Upon detecting radiation, detector 204 can generate signal 212 and pass it along to measuring electronics 208, which can generate measurement data 216. Similarly, upon detecting radiation, detector 206 can generate signal 214 and pass it along to measuring electronics 210, which can generate measurement data 218.

Referring to FIG. 2B, the exemplary array 250 can be arranged in π radians orientation (as opposed to the 0 radians orientation of the array shown in FIG. 2a) with respect to incident beam 201. Detector 204 and can now be positioned in an odd orientation and detector 206 is positioned in an even orientation with respect to the incident beam 201. Upon detecting radiation, detector 204 can generate signal 211 and pass it along to the measuring electronics 208, which can generate measurement data 215. Similarly, upon detecting radiation, the detector 206 can generate signal 213 and pass it along to the measuring electronics 210, which can generate measurement data 217.

FIGS. 3A and 3B illustrate alternate implementations, where detectors can be mounted on separate substrates or PCBs. Referring to FIG. 3A, exemplary array 350 can be arranged in 0 radians orientation (as opposed to π radians orientation of the array shown in FIG. 3B). As can be understood, similar to FIGS. 2A and 2B, the arrangements shown in FIGS. 3A and 3B are provided here for illustrative purposes only and are not intended to limit the present disclosure. The shown orientations can be based on an angle of incidence of a radiation beam. Array 350 can include a substrate (e.g., PCB) 320 that can be used to mount irradiating detector 306 and another substrate or PCB 322 that can be used to mount detector 304. As shown in FIG. 3A, substrates 320 and 322 can be arranged substantially parallel to one another, however, as can be understood, substrates 320, 322 can be arranged in any other desired fashion. Detector 304 can be mounted in an even orientation and detector 306 can be mounted in an odd orientation with respect to the incident beam 302. Detectors 304, 306 can be communicatively coupled to measuring electronics 308, 310, respectively. Upon detecting radiation, detector 304 can generate signal 312 and pass it along to measuring electronics 308, which can generate measurement data 316. Similarly, upon detecting radiation, detector 306 can generate signal 314 and pass it along to the measuring electronics 310, which can generate measurement data 318.

Referring to FIG. 3B, exemplary array 350 can be arranged in a π radian orientation (as opposed to 0 radians orientation of the array shown in FIG. 3A). Detector 304 can be mounted in an odd orientation and the detector 306 can be mounted in an even orientation with respect to incident beam 301. Upon detecting radiation, detector 304 can generate signal 311 and pass it along to the measuring electronics 308, which can generate measurement data 315. Similarly, upon detecting radiation, detector 306 can generate signal 313 and pass it along to measuring electronics 310, which can generate measurement data 317.

Using arrays 250, 350 shown in FIGS. 2A-B and/or FIGS. 3A-B, two array normalizations calculations can be performed. One array normalization calculation (otherwise known as an array calibration) can be performed using radiation incident normal to the array in one of the two possible normal orientations (e.g., FIG. 2A or 3A), and the other normalization calculation can be performed using radiation incident at the second orientation normal to the array, rotated π radians from the first orientation (e.g., FIG. 2B or 3B, respectively). The array normalization calculations can generate a correction matrix, whereby all detectors can have an invariant sensitivity in that orientation to the radiation (i.e., a function, a quantity, and/or a property that remains unchanged when a specified transformation is applied). Here, the quantity can be the measured charge from incident radiation after the transformation (correction factor) has been applied. In some exemplary implementations, array normalizations might not be necessary if nominal array sensitivity factors are known.

Based on the determined array normalizations (whether calculated or known), radiation dose distributions can be determined. In particular, application of two normalization arrays on a single measurement of a beam of radiation at any angle of incidence to the array can result in two possible dose distributions. These two dose distributions can correct for the even/odd parity orientations of the neighboring detectors. Two additional dose distributions can be determined by matching parity orientations in the normalization arrays and applying these equal parity arrays to the measurement array that has a mixed parity. The result can be a dose distribution that can have a portion of the detectors corrected with an even parity and the other portion of detectors corrected with an odd parity.

Based on the mixed parity dose calculation for the neighboring detectors, a dose difference between the neighboring detectors can be determined. The dose difference can be based on a detector's proximity to its neighbor detectors being in a low dose gradient region of the radiation field. The determined dose difference can be used to obtain information on the beam incident angle.

For example, referring to FIGS. 2A-B, the even orientation of detector X 204 (shown in FIG. 2A) can have an even normalization factor, while that same detector X (i.e., detector 204 shown in FIG. 2B) can have an odd normalization factor when it is oriented odd during an array normalization measurement. For an arbitrary measurement, detector X 204 can have two possible results after applying the array factor. Similarly, the odd orientation detector Y 206 can have an odd normalization factor, while it can have an even normalization factor when oriented even. Hence, the results for the detectors X and Y, respectively, would be as follows:

$r_{Xe} = m_X * e_{nf}$ $r_{Xo} = m_X * o_{nf}$ $r_{Ye} = m_Y * e_{nf}$ $r_{Yo} = m_Y * o_{nf}$ wherein r is result, e is even parity, o is odd parity, m is a measured value, nf is a normalization factor.

Because detectors X 204 and Y 206 are neighboring detectors in a region of zero and/or low dose gradient, the results $r_{Xe}$ and $r_{Yo}$ can have substantially similar or same values. Similarly, the results $r_{Xo}$ and $r_{Ye}$ can also have substantially similar or same values. However, the results $r_{Xe}$ and $r_{Ye}$ are not equivalent because while parities of their normalization factors match, their orientation parities in the beam do not. Similarly, the results $r_{Xo}$ and $r_{Yo}$ are not equivalent for the same reasons.

Figure 5:
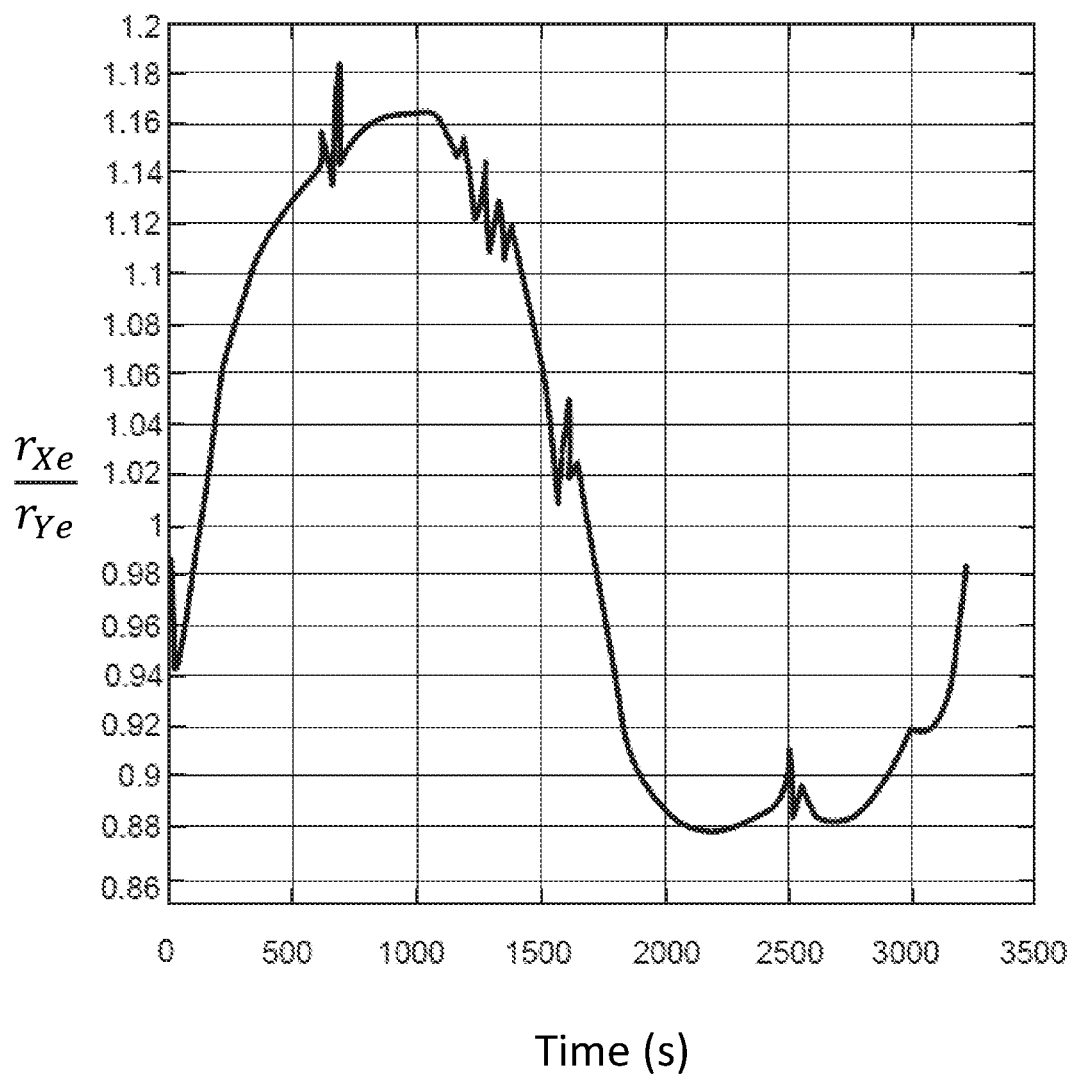
FIG. 5 illustrates an exemplary experimental detector response ratio of plot as a function of beam delivery time during rotation of the gantry according to some implementations of the current subject matter.

FIG. 4 illustrates an exemplary experimental detector response ratio plot as a function of gantry angle, according to an implementation of the current subject matter. FIG. 5 illustrates an exemplary experimental detector response ratio of plot as a function of beam delivery time during rotation of the gantry according to an implementation of the current subject matter. Plot 400 illustrates an exemplary transfer function from a dose difference (i.e., a detector response ratio) to gantry angle 122. Plot 500 illustrates a ratio $r_{Xe}/r_{Ye}$ as a function of beam delivery time as the gantry rotates. Though FIG. 4 and FIG. 5 are based on $r_{Xe}/r_{Ye}$, the ratio $r_{Xo}/r_{Yo}$ can be used as well. Based on the response differences at different times during the gantry rotation (as shown in FIG. 5), a gantry angle 122 can be determined using the transfer function shown in FIG. 4.

Figure 6:
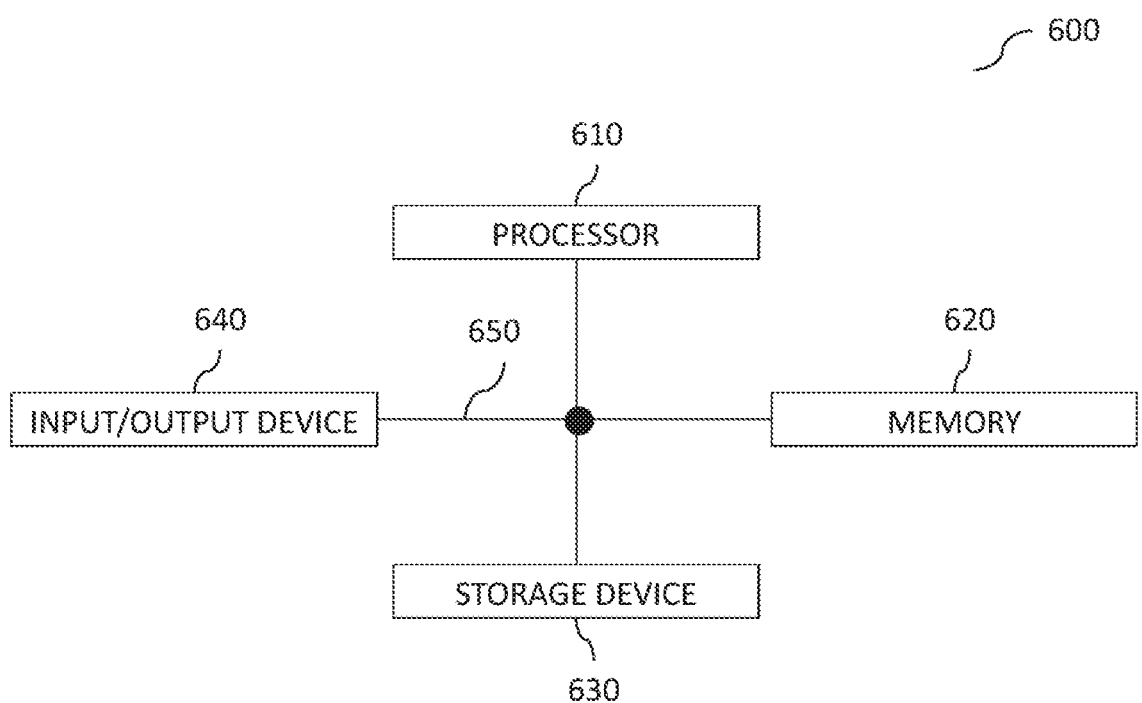
FIG. 6 illustrates an exemplary system according to some implementations of the current subject matter.

In some implementations, the current subject matter can be configured to be implemented in system 600, as shown in FIG. 6. System 600 can include one or more of a processor 610, a memory 620, a storage device 630, and an input/output device 640. Each of components 610, 620, 630 and 640 can be interconnected using system bus 650. Processor 610 can be configured to process instructions for execution within the system 600. In some implementations, processor 610 can be a single-threaded processor. In alternate implementations, processor 610 can be a multi-threaded processor. Processor 610 can be further configured to process instructions stored in memory 620 or on storage device 630, including receiving or sending information through the input/output device 640. Memory 620 can store information within system 600. In some implementations, memory 620 can be a computer-readable medium. In alternate implementations, memory 620 can be a volatile memory unit. In yet some implementations, memory 620 can be a non-volatile memory unit. Storage device 630 can be capable of providing mass storage for system 600. In some implementations, storage device 630 can be a computer-readable medium. In alternate implementations, storage device 630 can be a floppy disk device, a hard disk device, an optical disk device, a tape device, non-volatile solid-state memory, or any other type of storage device. The input/output device 640 can be configured to provide input/output operations for system 600. In some implementations, input/output device 640 can include a keyboard and/or pointing device. In alternate implementations, input/output device 640 can include a display unit for displaying graphical user interfaces.

In some implementations, control system 114 can be used to determine gantry angle 122 utilizing the systems and methods described herein. In other implementations, computer hardware, software and devices used to determine gantry angle 122 can be separate from control system 114. In still other implementations, both control system 114 and separate hardware, software and/or devices may be used together to determine gantry angle 122.

Figure 7:
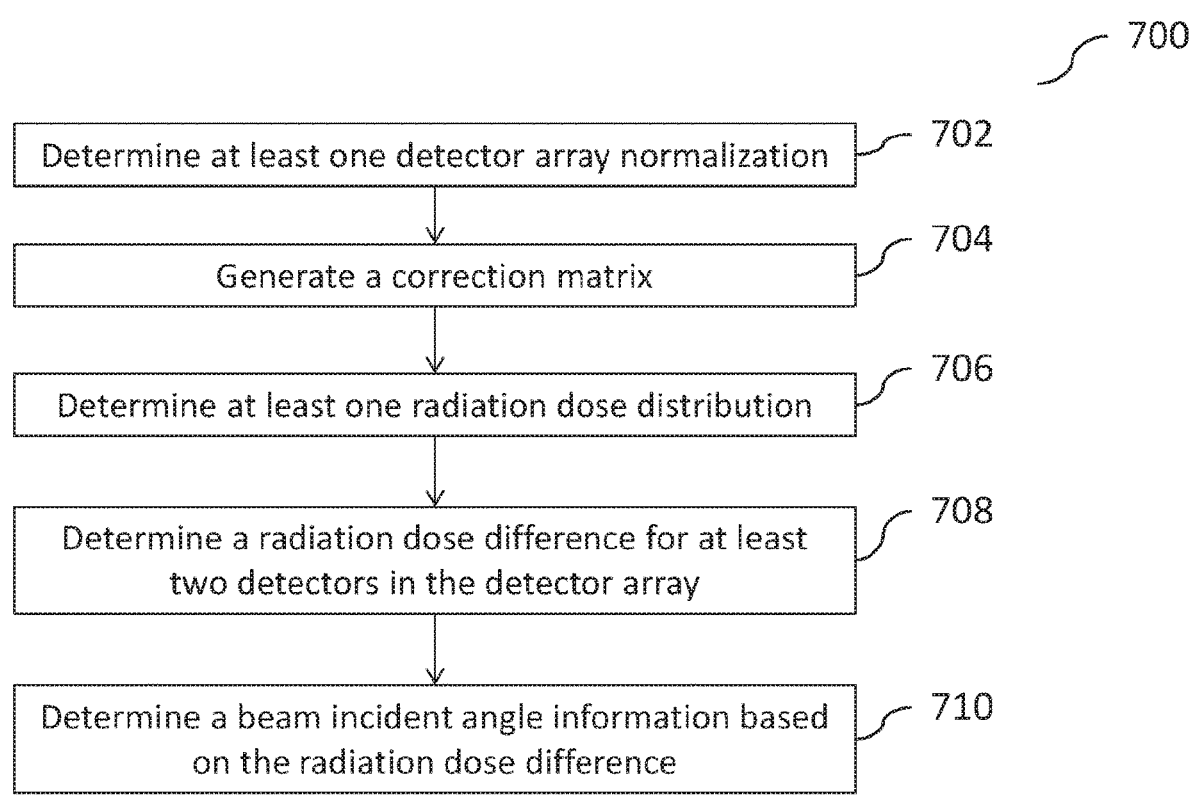
FIG. 7 illustrates an exemplary process according to some implementations of the current subject matter.

FIG. 7 illustrates an exemplary process 700 for determining a beam angle direction, according to some implementations of the current subject matter. At 702, at least one detector array normalization can be determined. The determination can be made using an array of neighboring detectors in a radiation system, where the detectors can be arranged in odd/even orientation with regard to an incident beam, where orientation of the detectors with respect to the incident beam can be rotated π radians to obtain different results. The determination can include calculation of array normalization or using known parameters. At 704, a correction matrix, based on the array normalizations, can be generated. At 706, the correction matrix can be applied to at least one measurement of a beam of radiation at any angle of incidence to determine at least one radiation dose distribution. At 708, using a mixed parity dose calculation, a radiation dose difference for at least two detectors in the detector array can be determined. At 710, beam incident angle information can be determined using the radiation dose difference, as determined at 708.

In other implementations, a method of determining gantry angle 122 can include performing at least one of the following: measuring a radiation response ratio between neighboring detectors versus gantry rotation angles, measuring an angular dependence of each detector versus gantry rotational angles, calculating a dose gradient for each beam angle during radiation measurement, calculating neighboring detector ratios in the low dose gradient region (e.g., an average for multiple ratios in a region), using the determined detector ratio to match a predefined detector ratio versus gantry angle curve and determine gantry angle 122, and using determined gantry angle 122 to match an angular response to gantry angle 122 for each detector while applying a correction factor to the angular response.

Figure 8:
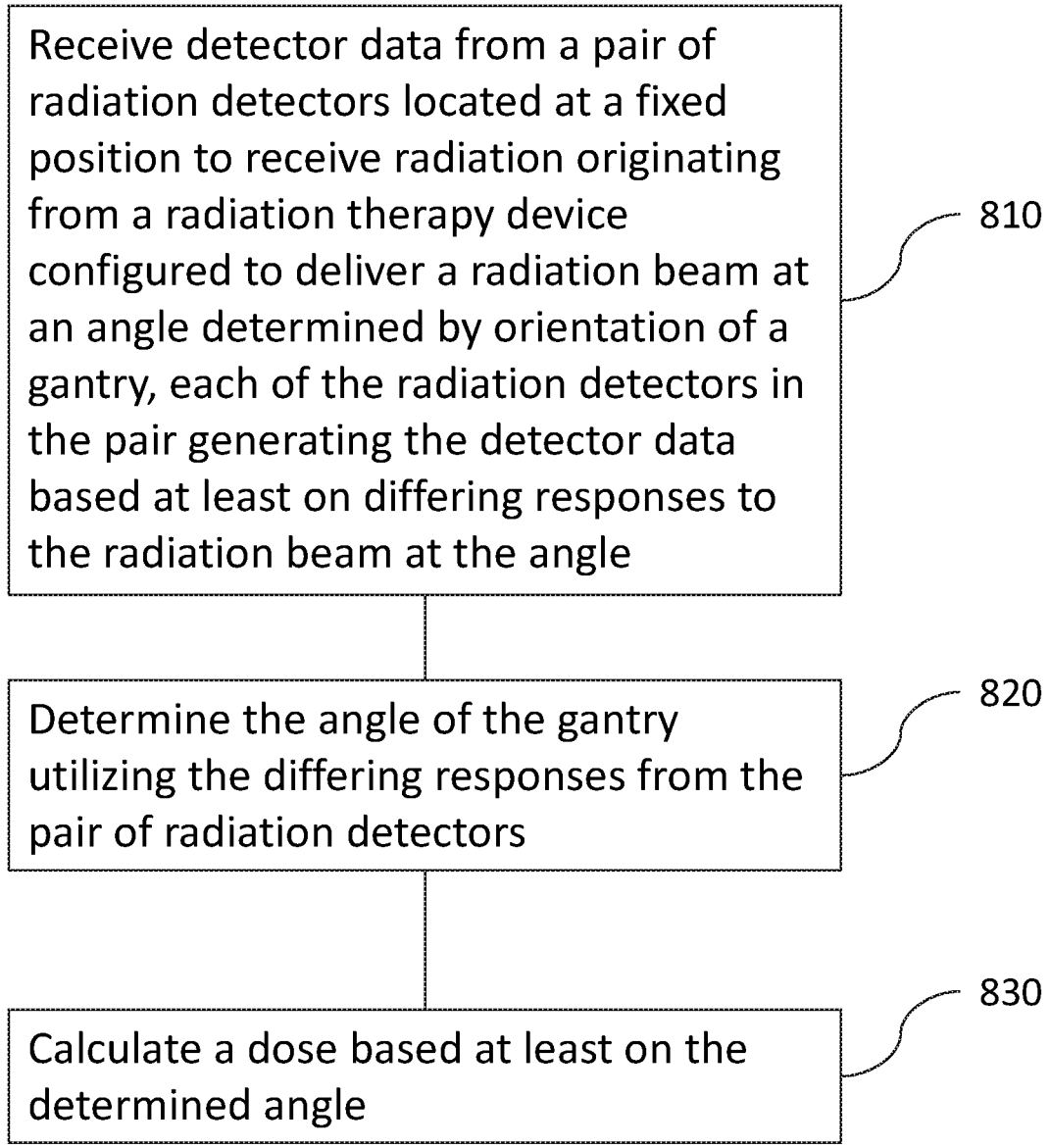
FIG. 8 illustrates another exemplary process according to some implementations of the current subject matter.

FIG. 8 illustrates another exemplary process according to some implementations of the current subject matter. In another implementation, a method, implemented by a programmable processor, and/or embedded as instructions in a non-transient, computer-readable medium, can include receiving detector data from a pair of radiation detectors. The pair of radiation detectors can be located at a fixed position to receive radiation originating from a radiation therapy device 102 configured to deliver a radiation beam 112 at an angle 122 determined by orientation of a gantry 104. Each of the radiation detectors in the pair can generate the detector data based at least on differing responses to radiation beam 112 at the angle 122. The method or instructions can also include determining the angle 122 of the gantry 104 utilizing the differing responses from the pair of radiation detectors. A dose may then be calculated based at least on determined angle 122.

The present disclosure contemplates that the calculations disclosed in the embodiments herein may be performed in a number of ways, applying the same concepts taught herein, and that such calculations are equivalent to the embodiments disclosed.

One or more aspects or features of the subject matter described herein can be realized in digital electronic circuitry, integrated circuitry, specially designed application specific integrated circuits (ASICs), field programmable gate arrays (FPGAs) computer hardware, firmware, software, and/or combinations thereof. These various aspects or features can include implementation in one or more computer programs that are executable and/or interpretable on a programmable system including at least one programmable processor, which can be special or general purpose, coupled to receive data and instructions from, and to transmit data and instructions to, a storage system, at least one input device, and at least one output device. The programmable system or computing system may include clients and servers. A client and server are generally remote from each other and typically interact through a communication network. The relationship of client and server arises by virtue of computer programs running on the respective computers and having a client-server relationship to each other.

These computer programs, which can also be referred to as programs, software, software applications, applications, components, or code, include machine instructions for a programmable processor, and can be implemented in a high-level procedural language, an object-oriented programming language, a functional programming language, a logical programming language, and/or in assembly/machine language. As used herein, the term "machine-readable medium" (or "computer readable medium") refers to any computer program product, apparatus and/or device, such as for example magnetic discs, optical disks, memory, and Programmable Logic Devices (PLDs), used to provide machine instructions and/or data to a programmable processor, including a machine-readable medium that receives machine instructions as a machine-readable signal. The term "machine-readable signal" (or "computer readable signal") refers to any signal used to provide machine instructions and/or data to a programmable processor. The machine-readable medium can store such machine instructions non-transitorily, such as for example as would a non-transient solid-state memory or a magnetic hard drive or any equivalent storage medium. The machine-readable medium can alternatively or additionally store such machine instructions in a transient manner, such as for example as would a processor cache or other random access memory associated with one or more physical processor cores.

To provide for interaction with a user, one or more aspects or features of the subject matter described herein can be implemented on a computer having a display device, such as for example a cathode ray tube (CRT) or a liquid crystal display (LCD) or a light emitting diode (LED) monitor for displaying information to the user and a keyboard and a pointing device, such as for example a mouse or a trackball, by which the user may provide input to the computer. Other kinds of devices can be used to provide for interaction with a user as well. For example, feedback provided to the user can be any form of sensory feedback, such as for example visual feedback, auditory feedback, or tactile feedback; and input from the user may be received in any form, including, but not limited to, acoustic, speech, or tactile input. Other possible input devices include, but are not limited to, touch screens or other touch-sensitive devices such as single or multi-point resistive or capacitive trackpads, voice recognition hardware and software, optical scanners, optical pointers, digital image capture devices and associated interpretation software, and the like.

In the descriptions above and in the claims, phrases such as "at least one of" or "one or more of" may occur followed by a conjunctive list of elements or features. The term "and/or" may also occur in a list of two or more elements or features. Unless otherwise implicitly or explicitly contradicted by the context in which it used, such a phrase is intended to mean any of the listed elements or features individually or any of the recited elements or features in combination with any of the other recited elements or features. For example, the phrases "at least one of A and B;" "one or more of A and B;" and "A and/or B" are each intended to mean "A alone, B alone, or A and B together." A similar interpretation is also intended for lists including three or more items. For example, the phrases "at least one of A, B, and C;" "one or more of A, B, and C;" and "A, B, and/or C" are each intended to mean "A alone, B alone, C alone, A and B together, A and C together, B and C together, or A and B and C together." Use of the term "based on," above and in the claims is intended to mean, "based at least in part on," such that an unrecited feature or element is also permissible.

The subject matter described herein can be embodied in systems, apparatus, methods, computer programs and/or articles depending on the desired configuration. Any methods or the logic flows depicted in the accompanying figures and/or described herein do not necessarily require the particular order shown, or sequential order, to achieve desirable results. The implementations set forth in the foregoing description do not represent all implementations consistent with the subject matter described herein. Instead, they are merely some examples consistent with aspects related to the described subject matter. Although a few variations have been described in detail above, other modifications or additions are possible. In particular, further features and/or variations can be provided in addition to those set forth herein. The implementations described above can be directed to various combinations and subcombinations of the disclosed features and/or combinations and subcombinations of further features noted above. Furthermore, above described advantages are not intended to limit the application of any issued claims to processes and structures accomplishing any or all of the advantages.

Additionally, section headings shall not limit or characterize the invention(s) set out in any claims that may issue from this disclosure. Specifically, and by way of example, although the headings refer to a "Technical Field," such claims should not be limited by the language chosen under this heading to describe the so-called technical field. Further, the description of a technology in the "Background" is not to be construed as an admission that technology is prior art to any invention(s) in this disclosure. Neither is the "Summary" to be considered as a characterization of the invention(s) set forth in issued claims. Furthermore, any reference to this disclosure in general or use of the word "invention" in the singular is not intended to imply any limitation on the scope of the claims set forth below. Multiple inventions may be set forth according to the limitations of the multiple claims issuing from this disclosure, and such claims accordingly define the invention(s), and their equivalents, that are protected thereby.

What is claimed is:

1. A system comprising:
    a radiation therapy device with a gantry, the radiation therapy device configured to deliver a radiation beam at an angle determined by orientation of the gantry;
    a pair of radiation detectors located at a fixed position to receive radiation originating from the radiation beam, each of the radiation detectors in the pair generating differing responses to the radiation beam at the angle; and
    computer hardware configured to perform operations comprising:
        determining the angle of the gantry utilizing the differing responses from the pair of radiation detectors.

2. The system of claim 1 wherein the computer hardware is further configured to display the determined angle, to compare the determined angle to a planned angle, or to use the determined angle in a dose calculation.

3. The system of claim 1 wherein the fixed position of the pair of radiation detectors is within the radiation beam.

4. The system of claim 1 wherein the fixed position of the pair of radiation detectors is outside of the radiation beam and the pair of radiation detectors detect scattered radiation.

5. The system of claim 1 wherein the pair of radiation detectors are mounted on a single substrate.

6. The system of claim 1 wherein the pair of radiation detectors are mounted on different substrates.

7. The system of claim 1 wherein the radiation detectors in the pair are oriented in opposite directions.

8. The system of claim 1 wherein the radiation detectors generate differing responses due to their orientation.

9. The system of claim 1 wherein the radiation detectors generate different responses due to the detectors being of different types.

10. The system of claim 1 wherein the radiation detectors generate different responses due to the placement of radiation absorbing material.

11. The system of claim 1 wherein the detectors are close together.

12. The system of claim 11 wherein a separation between the pair of radiation detectors is approximately 2.5 mm.

13. The system of claim 1, further comprising multiple pairs of radiation detectors, the determining based on the differing responses of multiple close together pairs of radiation detectors.

14. The system of claim 1, further comprising a flat array of radiation detectors including the pair of radiation detectors.

15. A computer program product comprising a non-transitory, machine-readable medium storing instructions which, when executed by at least one programmable processor, cause operations comprising:
    receiving responses from a pair of radiation detectors located at a fixed position that receive radiation originating from a radiation beam at an angle determined by orientation of a gantry, wherein each of the radiation detectors in the pair generate differing responses to the radiation beam at the angle; and
    determining the angle of the gantry utilizing the differing responses from the pair of radiation detectors.

16. The computer program product of claim 15, the determination of the angle further comprising measuring a radiation response ratio between neighboring detectors.

17. The computer program product of claim 16, the determination of the angle further comprising calculating a dose gradient of the radiation beam for the angle, wherein the radiation response ratio is calculated in a low gradient region of the radiation beam.

18. The computer program product of claim 17, the determination of the angle further comprising matching the radiation response ratio to a predefined detector ratio versus gantry angle curve.

19. The computer program product of claim 15, the operations further comprising:
    calculating a first array normalization based on radiation incident at a first direction normal to an array;
    calculating a second array normalization based on radiation incident at a second direction normal to the array but rotated pi radians from the first direction; and
    generating a correction matrix based on the first array normalization and the second array normalization, wherein application of the correction matrix results in detectors having an invariant sensitivity.

* * * * *